United States Patent
Mendonsa et al.

(10) Patent No.: US 11,990,184 B2
(45) Date of Patent: May 21, 2024

(54) DNA BACKBONE EDITING FOR DNA DATA STORAGE

(71) Applicant: Seagate Technology LLC, Fremont, CA (US)

(72) Inventors: Gemma Mendonsa, Minneapolis, MN (US); Riyan Alex Mendonsa, Minneapolis, MN (US); Tim Rausch, Farmington, MN (US)

(73) Assignee: SEAGATE TECHNOLOGY LLC, Fremont, CA (US)

( * ) Notice: Subject to any disclaimer, the term of this patent is extended or adjusted under 35 U.S.C. 154(b) by 510 days.

(21) Appl. No.: 17/031,664

(22) Filed: Sep. 24, 2020

(65) Prior Publication Data

US 2022/0090157 A1 Mar. 24, 2022

(51) Int. Cl.
*C12P 19/34* (2006.01)
*G11C 13/02* (2006.01)

(52) U.S. Cl.
CPC .............. *G11C 13/02* (2013.01); *C12P 19/34* (2013.01)

(58) Field of Classification Search
CPC . C12P 19/34; C12N 15/1089; C12N 2310/20; C12Q 2565/629; G11C 13/02
See application file for complete search history.

(56) References Cited

U.S. PATENT DOCUMENTS

| 9,384,320 | B2 | 7/2016 | Church et al. |
| 10,669,558 | B2 | 6/2020 | Ganjam |
| 2015/0004627 | A1* | 1/2015 | Wu .......................... C12Q 1/006 435/7.1 |
| 2020/0224207 | A1* | 7/2020 | Suetsugu et al. ....... C12N 15/66 |
| 2021/0277385 | A1* | 9/2021 | Suetsugu ............. C12Q 1/6844 |
| 2021/0332356 | A1* | 10/2021 | Popma ................... C12N 15/87 |
| 2021/0355819 | A1* | 11/2021 | Jones ...................... E21B 47/12 |

FOREIGN PATENT DOCUMENTS

| WO | 2017142999 A2 | 8/2017 |
| WO | WO-2018118998 A1 * | 6/2018 |
| WO | WO 2019/009361 * | 1/2019 |

OTHER PUBLICATIONS

Wang et al. "ExoCET: exonuclease in vitro assembly combined with RecET recombination for highly efficient direct DNA cloning from complex genomes" Nucleic Acids Research, 2018, vol. 46, No. 5, e28, published online Dec. 12, 2017, 11 pages; doi: 10.1093/nar/gkx1249 (Year: 2018).*

* cited by examiner

*Primary Examiner* — Jeremy C Flinders
(74) *Attorney, Agent, or Firm* — HOLZER PATEL DRENNAN (57) ABSTRACT

Methods of writing data to a DNA strand by inserting data-encoding oligos or symbols into a DNA backbone. One particular method of synthesizing a DNA strand encoding data includes cleaving a DNA backbone into multiple segments, and pasting a plurality of data-encoding oligo symbols between the multiple segments, with the terminal ends of the segments joining homologous terminal ends of the symbols, resulting in the DNA strand encoding data comprising alternating segments and symbols.

8 Claims, 5 Drawing Sheets

TCGATTC
AGCTAAG

/— 200a
TCGATTCGG
TTAGCTAAG

/— 200b
TCGATTCGA
TTAGCTAAG

/— 200c
TCGATTCGG
TCAGCTAAG

/— 200d
TCGATTCAG
TCAGCTAAG

/— 200e
TCGATTCGT
TAAGCTAAG

/— 200f
TCGATTCGC
TGAGCTAAG

DNA BACKBONE EDITING FOR DNA DATA STORAGE

BACKGROUND

DNA is an emerging technology for data storage. DNA is used as a storage medium by converting binary code (0 and 1) to genetic code (A, C, G, T). The converted code can be synthesized into DNA molecules, which are then stored until read.

Current methods assert that a DNA strand or gene, to store 5 KB of data, can be written in 14 days. Comparatively, magnetic disk drives and magnetic tapes both can write 1 TByte in about an hour. A single DNA base pair location can store 2 bits; thus, 4000 Giga-base pairs would need to be stored in an hour to match the capabilities of a single disk drive or tape. Although current technology is believed to be capable of writing 15 base pairs an hour, there needs to be an 8 to 9 order of magnitude improvement in order for DNA data storage to be viable.

SUMMARY

This disclosure is directed to methods of writing data to a DNA strand by inserting data-encoding oligos into a DNA backbone.

One particular implementation described herein is a method of synthesizing a DNA strand encoding data. The method includes cleaving a DNA backbone into multiple segments (e.g., at least three segments), each of the multiple segments having terminal ends, and pasting a plurality of data-encoding symbols having terminal ends between the multiple segments, with the terminal ends of the segments joining homologous terminal ends of the symbols, resulting in the DNA strand encoding data comprising alternating segments and symbols. The method may further include cleaving the DNA strand encoding data comprising alternating segments and symbols into multiple second segments, each of the multiple second segments having terminal ends, and pasting a second plurality of data-encoding symbols having terminal ends between the multiple second segments, with the terminating ends of the second segments joining homologous terminal ends of the second symbols, resulting in a second DNA strand encoding data.

Another particular implementation described herein is a method that includes cleaving a DNA backbone into multiple segments by moving, via voltage, at least one of the DNA backbone and a Cas9 across a hydrophobic fluidic platform and combining on the platform the DNA backbone and the Cas9 resulting in the multiple segments each having terminal ends; and moving across the platform, via voltage, a plurality of data-encoding symbols having terminal ends on the platform and inserting the symbols between the multiple segments, with the terminal ends of the segments joining homologous terminal ends of the symbols, forming the DNA strand encoding data comprising alternating segments and symbols.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. These and various other features and advantages will be apparent from a reading of the following detailed description.

BRIEF DESCRIPTION OF THE DRAWING

The described technology is best understood from the following Detailed Description describing various implementations read in connection with the accompanying drawing.

DETAILED DESCRIPTION

The amount of data generated by the global population is far greater than the amount of data storage space available. DNA is an incredibly compact data storage medium and is stable for many years in mild storage conditions. By converting binary code (0 and 1) to genetic code (A, C, G, T; as an example, A=00, C=10, G=01, and T=11), a DNA strand can be a biological storage media to hold the code.

As indicated above, various methods described herein edit a DNA backbone by inserting predetermined DNA symbols at intervals along the length of the backbone. A DNA symbol is an oligo, a short sequence of DNA (e.g., 1-20 bases) that encodes a unique segment of binary code. Alternately, a string of multiple nucleotides or a string of multiple symbols can be inserted. To insert a DNA nucleotide, symbol, or string of symbols into a DNA backbone, the backbone is cut in the desired insertion location and the nucleotide(s), symbol, or string of symbols is then pasted into the cut backbone. The methods allow the DNA code to be written in a massively parallel manner.

In the following description, reference is made to the accompanying drawing that forms a part hereof and in which is shown by way of illustration at least one specific implementation. The following description provides additional specific implementations. It is to be understood that other implementations are contemplated and may be made without departing from the scope or spirit of the present disclosure. The following detailed description, therefore, is not to be taken in a limiting sense. While the present disclosure is not so limited, an appreciation of various aspects of the disclosure will be gained through a discussion of the examples, including the figures, provided below. In some instances, a reference numeral may have an associated sub-label consisting of a lower-case letter to denote one of multiple similar components. When reference is made to a reference numeral without specification of a sub-label, the reference is intended to refer to all such multiple similar components.

As indicated above, for a data storage gene, each nucleotide is assigned a bit pattern; in one example, A=00, C=10, G=01, and T=11. In general, when an oligo is used in a data storage gene, the term "symbol" is used to represent the oligo that has a bit pattern. It is this "symbol" that is inserted into the DNA backbone. A symbol consists of a DNA sequence containing two linking ends with a base symbol between them. The base symbol is a DNA sequence (e.g., 1-20 pairs of nucleotides) that can be translated to a short sequence of binary code. There may be hundreds to thousands of different base symbols, depending on the length of the symbol.

In some implementations, other or additional information may be carried by the symbol. For example, the symbol may carry metadata, such as a timing indicator.

Figure 1A:
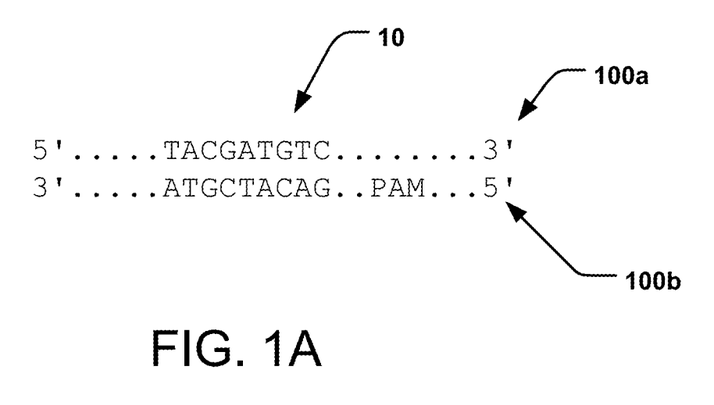
FIG. 1A is a schematic rendering of an example DNA double strand.

In FIG. 1A, a schematic double strand DNA 10 is shown, calling out a first strand 100a comprising nucleotides located between the 3' end and the 5' end and a complementary second strand 100b comprising complementary nucleotides located between the 5' end and the 3' end. The second strand 100b is shown having a PAM sequence, which is a marker indicating a specific nucleotide sequence immediately following the target sequence. The PAM sequence is not part of the target sequence but is just downstream of the target sequence and indicates the relative location of the Cas9 activity. Even with the appropriate gRNA, if the PAM is not found, the Cas9 will not cleave the DNA. Similarly, if a PAM is found but a match for the gRNA is not found, the Cas9 will not cleave the DNA.

The DNA strand 10 shown is merely an example and does not represent any organism, as it is well known that DNA strands are significantly longer and that any nucleotide sequence may be present. The DNA backbone may be portions of, or the entirety of, e.g., a prokaryotic genome, a eukaryotic genome, a synthetic genome, or any combination thereof.

As described above, the present disclosure provides for editing of a DNA strand for the purpose of data storage by inserting DNA symbols at intervals along the length of the DNA backbone (e.g., into the DNA strand 10). Specific biomolecules can cut either one or both strands of the DNA strand 10 at certain sequences. One of the more well-known DNA cleavage biomolecules is the Cas9 protein. The Cas9 protein is used together with a piece of RNA called a guide RNA (gRNA) that contains the desired target sequence to be cut. Other known DNA cleavage mechanisms are CRISPR/Cas (Clustered, Regularly Interspaced, Short Palindromic Repeats and CRISPR-associated) systems, *Pyrococcus furiosus* Argonaute (Pfago), TALEN (Transcription Activator-Like Effector Nuclease), restriction enzymes, zinc finger nucleases (ZFNs), or any biomolecule that can cleave DNA at a specific sequence.

When the Cas9 protein is mixed with the gRNA, the gRNA threads itself into the Cas9 protein. Because the gRNA contains the complementary sequence to the desired target sequence to be cut, the resulting Cas9-gRNA mixture searches the backbone of the DNA strand 10 for the PAM and a sequence matching its target gRNA. When it finds a match, the Cas9 cuts both strands of the DNA strand.

Figure 1B:
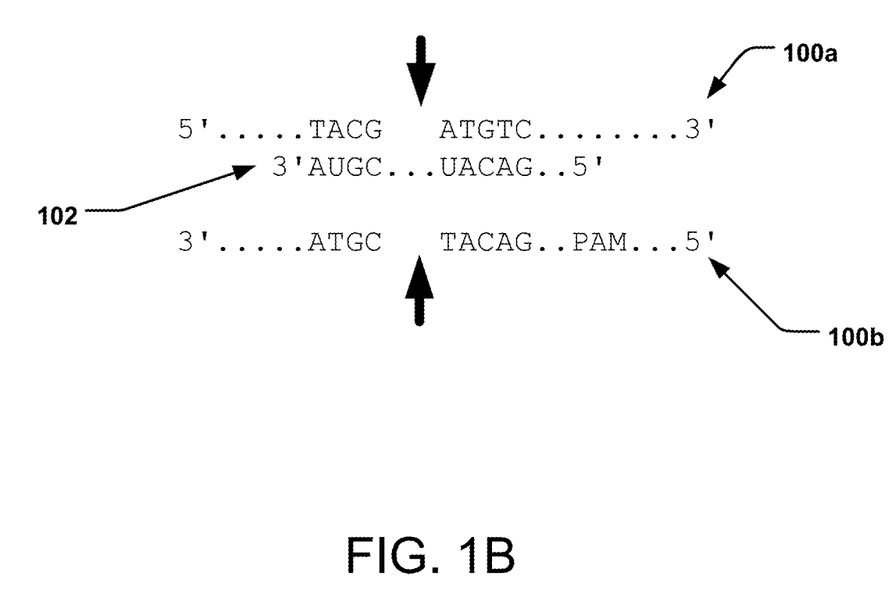
FIG. 1B is a schematic rendering of the DNA double strand cleaved with a gRNA strand threaded therein.

FIG. 1B illustrates a process of cutting the DNA strand 10 by inserting a guide RNA (gRNA) strand threaded into a Cas9 protein (the combined molecule shown as 102). When the gRNA strand binds to the DNA strand 10, the attached Cas9 cuts the DNA strand 10 to form two strands 100a, 100b, the cleavage area indicated by the arrows. After cleaving the strands 100a, 100b, the gRNA strand and the complexed Cas9 protein 102 releases, leaving the cleaved strands 100a, 100b.

The DNA strand 10 and strands 100a, 100b in FIG. 1A and the gRNA strand 102 of FIG. 1B are shown in significantly simplified form to merely to provide the basis for the methods of this disclosure.

Figure 2A:
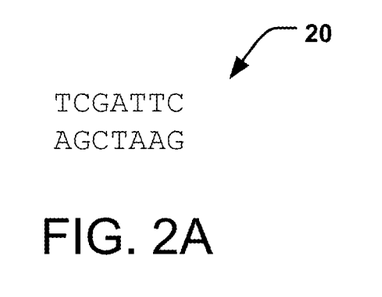
FIG. 2A is a schematic rendering of an example DNA oligo symbol.

As indicated above, a data-encoding oligo or symbol is inserted into the cleaved DNA strand. FIG. 2A illustrates an example of an oligo or base symbol 20 that encodes data. Using the example above where A=00, C=10, G=01, and T=11, the base symbol 20 represents 111001001111110 in the top strand. The bottom strand is complementary to the top strand and generally does not encode any additional data; if any data were encoded in the bottom strand, it would generally be duplicative of the top strand. The base symbol 20 may be inserted into different locations on the backbone by attaching different linking ends to the base symbol 20.

A cut DNA strand, such as that shown in FIG. 1B, can be repaired by pasting in a DNA symbol that represents data, e.g., the base symbol 20.

To insert or paste the data-encoding symbol 20 into the cut DNA strand, the symbol 20 must have sequences at both ends that are complementary to the cut ends of the DNA backbone. The symbol 20 may be a full double strand, as shown in FIG. 2A, with blunt ends. In other implementations, the symbol may have chewed-back or overhanging ends that are complementary to overhanging ends on the cut DNA strand. Overhanging ends can be generated by digestion with an exonuclease or an endonuclease.

Figure 2B:
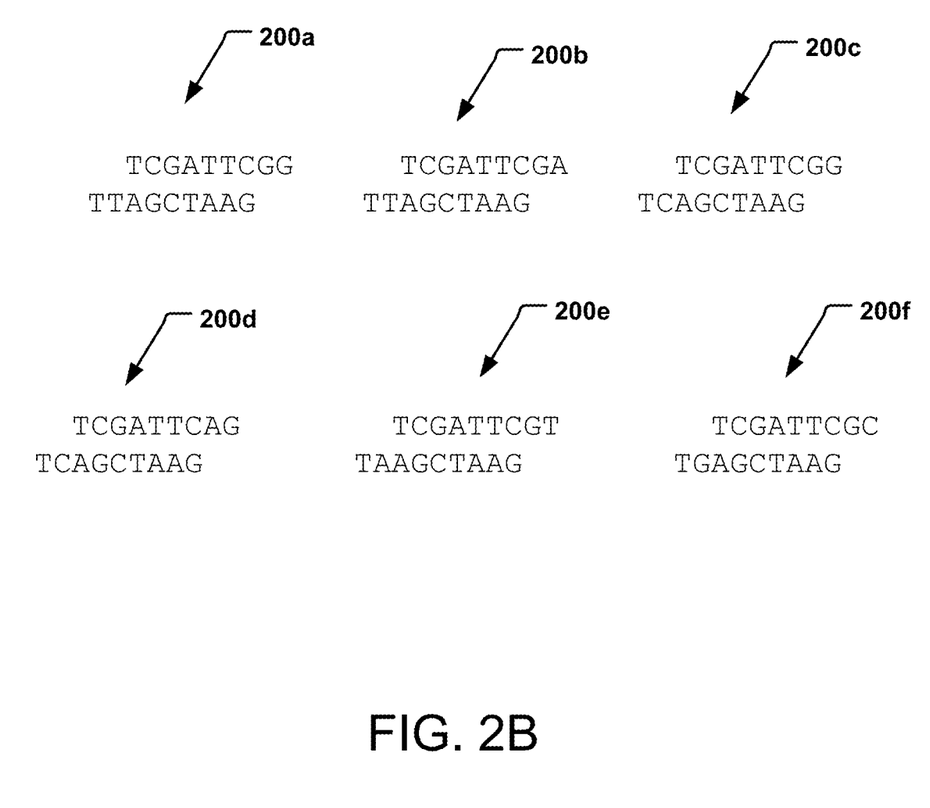
FIG. 2B is a schematic rendering of the DNA oligo symbol having six different hanging ends added thereto.

Different overhanging linking ends are shown added to the base symbol 20 in FIG. 2B resulting in the exemplary symbols 200a, 200b, 200c, 200d, 200e, 200f. Each of these symbols 200 has the same base symbol (the base symbol 20) with different linking ends. In the particular example shown, each overhanging end is only two nucleotides; other examples of hanging ends can be shorter or longer, in most implementations however, longer. The sequences on the ends of the symbols are complementary to defined regions of the cut backbone.

Ends that are complementary can be joined together, e.g., via a homology-directed repair (HDR) process; in such a manner, a symbol 200 can be inserted into the cleaved DNA strand or backbone. Any HDR can be done via, e.g., Gibson assembly, restriction digest and ligation, ligase-independent cloning, sequence- and ligase-independent cloning, a "Golden Gate" method, Zero-Background Redα method, Hot Fusion method, BioBrick assembly, Seamless Ligation Cloning Extract method, overlap extension polymerase chain reaction, or other DNA assembly or cloning method. The resulting repaired DNA backbone now contains the desired inserted symbol(s).

The data-encoding symbols 20 and the symbols 200 having the linking ends, plus many others, can form a symbol library. Libraries of the base symbols 20 with every possible combination of linking ends (e.g., some of which are shown as the symbol 200) may be created and stored until assembly.

Symbols with different linking ends, such as the symbols 200, may be generated and stored in two different ways. In one implementation, base symbols with each possible combination of linking ends are synthesized and stored in a library for later use. In another implementation, symbols with different linking ends are created by attaching the desired terminal linking ends to the desired base symbols on-demand. With either method, the base symbols are inserted or pasted into a cleaved DNA strand.

Figure 3A:
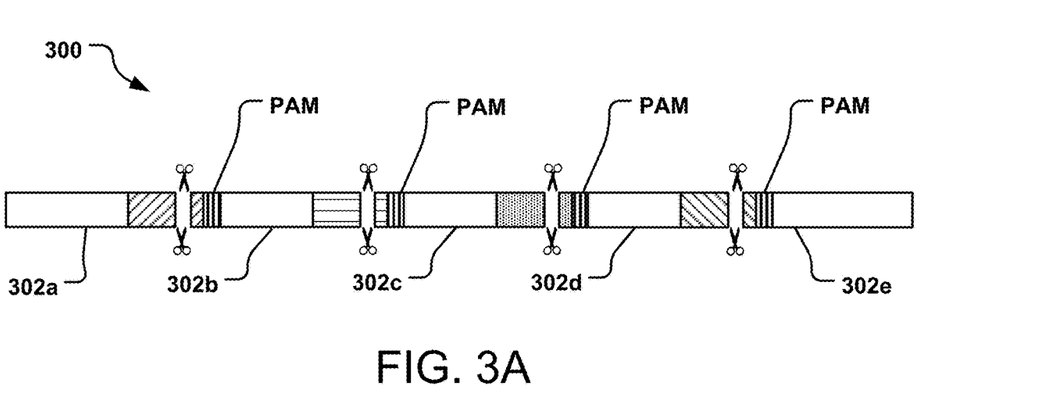
FIG. 3A is a schematic diagram of a first step in an example method of inserting data-encoding oligo symbols into a DNA backbone.
Figure 3B:
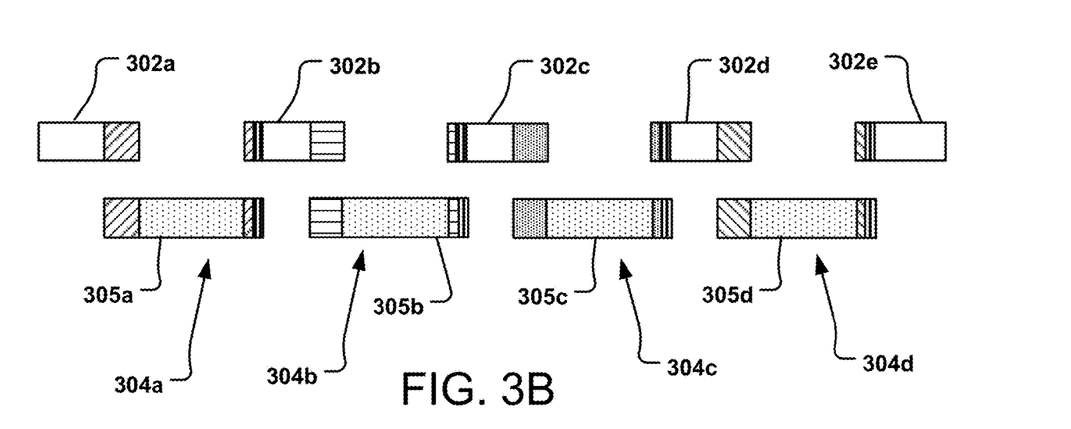
FIG. 3B is a schematic diagram of a second step in the example method.
Figure 3C:
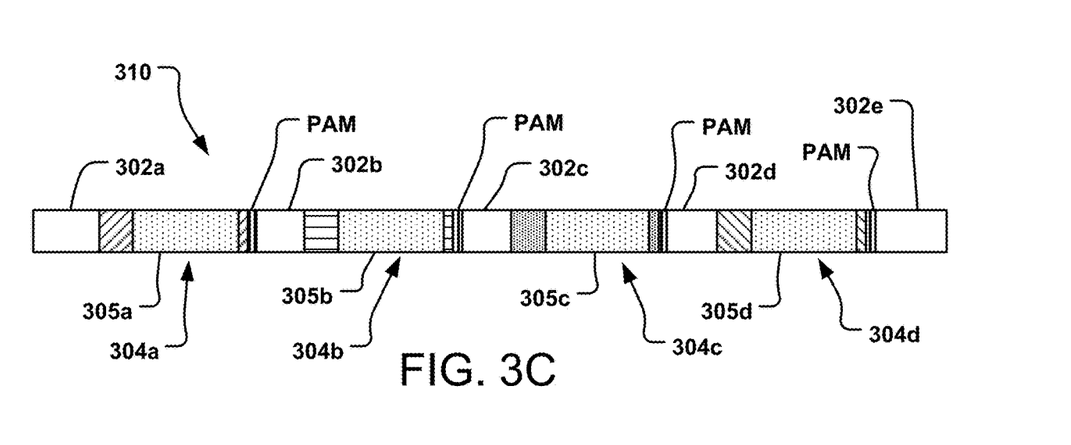
FIG. 3C is a schematic diagram of a third step in the example method.

FIGS. 3A, 3B and 3C schematically and stepwise show one implementation of a process for inserting encoded DNA symbols into a DNA strand or backbone to form a data storage strand by using already prepared symbols composed of base symbols with linking ends present.

In FIG. 3A, a DNA backbone 300 is cleaved at four specific, unique and different sequence addresses, each proximate a PAM (depicted as vertical stripes), resulting in five backbone segments 302. The result is a first segment 302a, a second segment 302b, a third segment 302c, a fourth segment 302d and a fifth segment 302e. Although in this example the DNA backbone 300 is cleaved into five segments 302, in other implementations the backbone 300 may be cleaved into, e.g., 3 to 100 segments, or even more than 100 segments. Typically, the backbone 300 is cleaved into at least 3 segments, or at least 5 segments, or at least 10 segments, or at least 20 segments, this cleaving being from the same process and being essentially simultaneously rather than sequentially.

The specific sequence addresses where the cleaving occurred are now split between adjacent segments 300. For example, the sequence that identified the first cleavage location (depicted as diagonal hatching) resulting in the first segment 302a and the second segment 302b is now split between the first segment 302a and the second segment 302b; the sequence that identified the second cleavage location (depicted as horizontal lines) resulting in the second segment 302b and the third segment 302c is now split between the second segment 302b and the third segment 302c, etc.

In FIG. 3B, the DNA symbols encoding data and containing ends homologous to the cleaved DNA backbone are introduced to the segments 302. The five segments 302a, 302b, 302c, 302d, 302e are shown in FIG. 3B with a data-encoding symbol 304 positioned proximate each cleavage location; specifically, a first symbol 304a is positioned to be bound to the first segment 302a and the second segment 302b, a second symbol 304b is positioned to be bound to the second segment 302b and the third segment 302c, a third symbol 304c is positioned to be bound to the third segment 302c and the fourth segment 302d, and a fourth symbol 304d is positioned to be bound to the fourth segment 302d and the fifth segment 302e. Each of the symbols 304 has a data-encoding base symbol 305 and ends that are complementary to the cleaved backbone so as to link the symbol 304 to the segments 302; specifically, the first symbol 304a has a first base symbol 305a, the second symbol 304b has a second base symbol 305b, the third symbol 304c has a third base symbol 305c and the fourth symbol 304d has a fourth base symbol 305d. The base symbol 305 may be the same or different from one symbol 304 to the other, however, the base symbol 305 is selected to provide the desired data bits. For example, there may be hundreds to thousands of different symbols 304 and different base symbols 305. The number of base symbols 305 may be the same or different as the number of symbols 304; as an example, FIG. 2A shows one base symbol 20 used to form six different symbols 200 in FIG. 2B, by changing the terminal ends.

In some implementations, more than one symbol 304 may be positioned between two segments 302. For example, two different symbols 304, with homologous terminal ends, may be inserted adjoining each other between two segments 302. If needed, an additional nucleotide or oligo may be included to facilitate the insertion of the multiple symbols 304.

It is noted that in this example there are four symbols 304 (and four base symbols 305) and five segments 302, so that the number of symbols 304 is one less than the number of segments 302. In other implementations, the number of symbols 304 can be greater than the number of segments 302. In such an implementation, more than one symbol 304 can be inserted in one location between adjacent segments 302. In another such implementation, one or more symbols 304 may be added to an end of the backbone, rather than at a cleaved location.

Homologous repair is shown in FIG. 3C to stitch the data-carrying symbols 304 and cleaved backbone segments 302 together. The resulting structure is a data storage strand 310 having the data-encoding base symbols 305 each located proximate a PAM in the DNA backbone.

It is noted that multiple processes may be done in series or in parallel (e.g., cleaving multiple backbones at a time, etc.) to increase the rate of synthesis of a large file of data.

FIGS. 4A, 4B, 4C and 4D schematically and stepwise show another implementation of a process for inserting encoded DNA symbols into a DNA strand or backbone to form a data storage strand. In this process, the symbols with different linking ends are created by attaching of desired terminal linking ends to the desired base symbols on-demand. A base symbol encoding the desired data bits is selected from a library, and the desired linking ends are selected from a second library. The linking ends and the base symbols contain a small homologous region to enable their joining via HDR. Assembling base symbols and linking ends on-demand reduces the required library size and simplifies liquid handling.

Figure 4A:
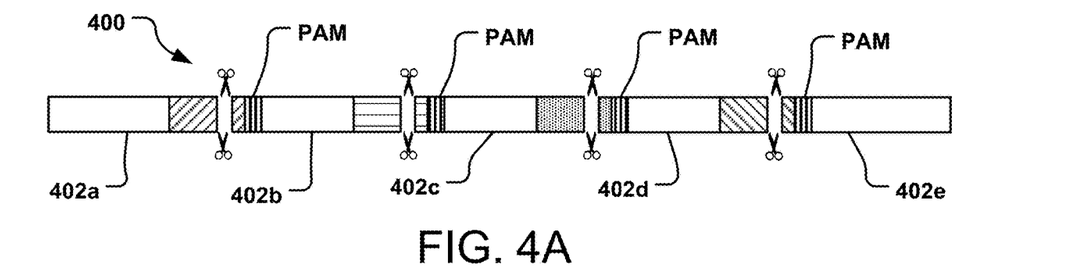
FIG. 4A is a schematic diagram of a first step in another example method of inserting data-encoding oligo symbols into a DNA backbone.

In FIG. 4A, as in the previous process, a DNA backbone 400 is cleaved at four, specific, unique and different sequence addresses, each proximate a PAM (depicted as vertical stripes), resulting in five backbone segments 402. The result is a first segment 402a, a second segment 402b, a third segment 402c, a fourth segment 402d and a fifth segment 402e. The specific sequence addresses, where the cleaving occurred, are now split between adjacent segments 402. For example, the sequence that identified the first cleavage location (depicted as diagonal hatching) resulting in the first segment 402a and the second segment 402b is now split between the first segment 402a and the second segment 402b.

Figure 4B:
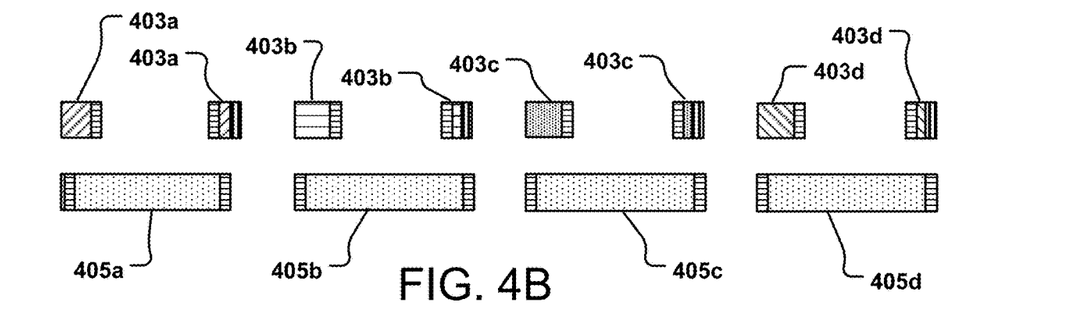
FIG. 4B is a schematic diagram of a second step in the example method.

In FIG. 4B, four base symbols 405a, 405b, 405c, 405d encoding the desired data are shown; the base symbols 405 may be the same or different but are selected to provide the desired data bits. Also shown are linking terminal ends 403 for attachment to the base symbols 405; each base symbol 405 has two linking ends 403, one for each end. Specifically, the first base symbol 405a has first linking ends 403a, the second base symbol 405b has second linking ends 403b, the third base symbol 405c has third linking ends 403c, and the fourth base symbol 405d has fourth linking ends 403d. These linking ends 403 may be held in a library formed of numerous oligos and selected based on the nucleotides needed to provide the engagement between the base symbols 405 and the segments 402.

When combined, the base symbols 405 and the linking ends 403 form a symbol 404 (called out in FIG. 4C); thus, each of the symbols 404 has one data-encoding base symbol 405 and ends 403 that are complementary to the cleaved backbone segments so as to link the symbol 404 to the segments 402. Specifically, the first base symbol 405a links to the first ends 403a, the second base symbol 405b links to the second ends 403b, the third base symbol 405c links to the third ends 403c, and the fourth base symbol 405d links to the fourth ends 403d.

Figure 4C:
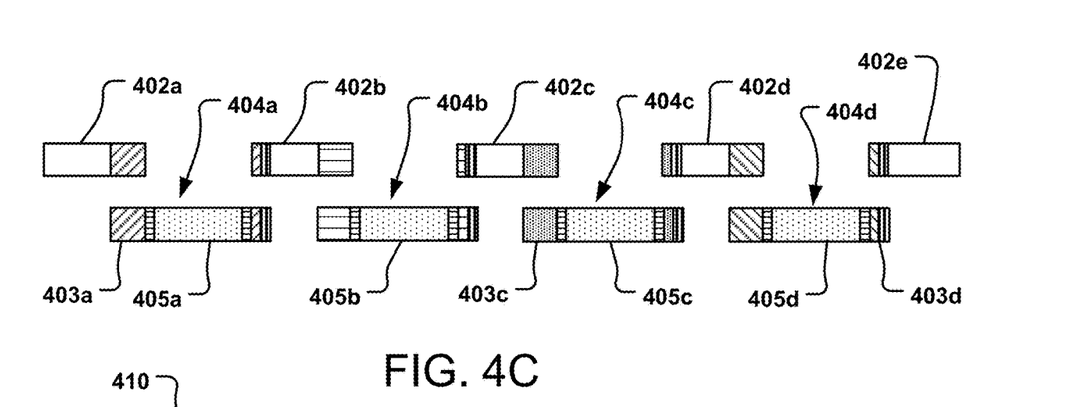
FIG. 4C is a schematic diagram of a third step in the example method.

In FIG. 4C, the resulting symbols 404, composed of the DNA base symbols encoding data linked to the linking ends, are introduced to the backbone segments. The five segments 402a, 402b, 402c, 402d, 402e are shown with a data-encoding symbol 404 positioned proximate each cleavage location; specifically, a first symbol 404a is positioned to be bound to the first segment 402a and the second segment 402b, a second symbol 404b is positioned to be bound to the second segment 402b and the third segment 402c, a third symbol 404c is positioned to be bound to the third segment 402c and the fourth segment 402d, and a fourth symbol 404d is positioned to be bound to the fourth segment 402d and the fifth segment 402e. Each of the symbols 404 has the base symbol 405 and the linking ends 403.

Figure 4D:
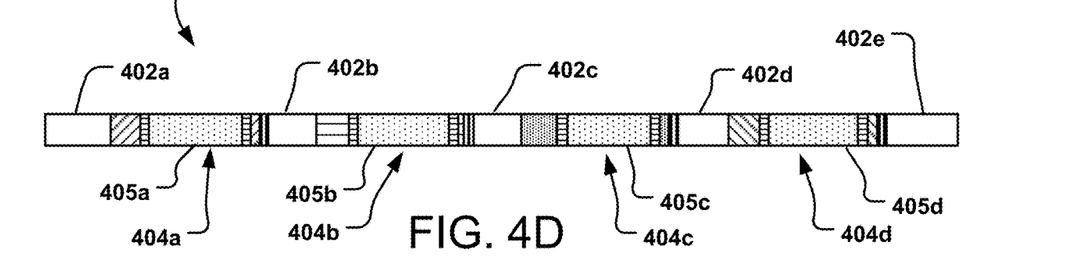
FIG. 4D is a schematic diagram of a fourth step in the example method.

The resulting structure is a data storage strand 410 in FIG. 4D having the data-encoding base symbols 405 located proximate a PAM in the DNA backbone.

The data storage strands 310, 410 can be read by any suitable mechanism to identify (sequence) the nucleotides and decipher the data.

Alternately, these data storage strands 310, 410 can undergo an additional cut-and-paste operation, such as shown in FIGS. 3A-3D and/or FIGS. 4A-4D to insert additional data-encoding symbols. These subsequent insertion points may be within a strand of the original backbone 300, 400 or may be within the symbols 304, 404 that were previously added to the original backbone 300, 400. The same or different DNA strand cleaving methodology (e.g., Cas9) may be used for any subsequent or additional operation.

By knowing the relative location of the data storage base symbols 305, 405 in relation to a marker, such as the PAM, the data can be read from the DNA strand by any suitable means. Alternately, any of the backbone segment, the backbone segment plus linking ends, or any linking ends can be markers identifying the location of the data. In addition to including a marker, the DNA backbone can carry additional information such as time stamps, indexes, or other formatting to aid in computational based tasks.

The previous discussion has provided an example utilizing a library of data-encoding symbols and a library of linking ends to form a DNA strand having the data-encoding symbols positioned in the strand in an arranged desired order. By utilizing multiple symbols and multiple linking ends, all of which are predetermined oligos, and utilizing parallel reactions, the synthesis rate of the final DNA data strand can be greatly improved compared to a de novo gene synthesis where each nucleotide is added one at a time.

In such a manner, content (e.g., a document, a picture) can be saved as data on DNA. The content can be written on one or more DNA strands or backbones; if multiple strands or backbones are used, they do not need to be similar in length or in content. DNA strands or backbones with different data written to them, that are part of the same file, can be mixed together or stored separately. This process can be repeated, e.g., by cutting the symbols that have been inserted, and inserting into the cut location a second (e.g., different) symbol.

The backbone cleaving synthesis methods described above can be implemented in any manner, e.g., utilizing various reactors, flasks, beakers, etc. The method is also particularly suited to be done as a microfluidic lab-on-a-chip process.

Lab-on-a-chip is a common term for an integrated circuit ("chip") on which one or several laboratory functions or chemical reactions are done. The chip can be no more than a few square centimeters. Labs-on-a-chip handle extremely small fluid volumes (e.g., measured as pico-liters) and are often called microfluidic systems. In digital microfluidics, the lab-on-a-chip has a hydrophobic "chip platform" on which fluid droplets (e.g., liquid droplets) can be manipulated by precisely controlled voltage application. The platform may have a cover plate covering the fluidic area. By utilizing the feature of surface tension of the fluid on the platform, the fluid can be precisely moved across the platform by voltage applied to the platform, e.g., in a grid.

For the synthesis methods described above, the lab-on-a-chip is operably and fluidically connected to the ingredients or components (e.g., the DNA backbone, the Cas9 protein and the gRNA, or the Cas9-gRNA mixture, and the symbols for the first method described above in relation to FIGS. 3A, 3B and 3C, or the DNA backbone, the Cas9 protein and the gRNA, or the Cas9-gRNA mixture, the base symbols, and the linking ends for the second method described above in relation to FIGS. 4A, 4B, 4C and 4D). Each of the components is retained in a well or other liquid storage compartment. In some designs, there may be only one well for the DNA backbone, one well for the Cas9-gRNA mixture, at least 10,000 wells for the symbols, or at least 20,000, or at least 30,000 wells, or at least 65,000 wells. Additionally or alternately, there can be at least 120 wells for the linking ends, or at least 30 wells, or at least 60 wells.

Using known techniques (e.g., voltage differential on the platform), the dispensed components (e.g., DNA backbone, base symbols, etc.) are moved on (across) the platform and mixed in the desired steps. All mixing of the components can be done on the platform or a dedicated mixing station may be used for one or more of the steps, e.g., utilizing heat and/or agitation, e.g., for cleaving the DNA backbone with the Cas9 and gRNA. In some implementations, the platform may include a controllable reaction facilitator, such as a UV light source, and/or the final mixing station may include a voltage source, e.g., to align the completed data encoded strand to aid in collection.

One suitable (physical) size for a lab-on-a-chip is about 20 mm by 20 mm, which is compatible to an 8 inch wafer and could have 785,000 array elements, each array element having controllable voltage independently applied thereto. In some implementations, each well or other storage compartment is 10× the size of an array element. This would provide 66,560 wells and leave 119,000 arrays for transport and mixing of the components on the platform.

A stacked or otherwise three-dimensional array of labs-on-a-chip would increase density and decrease required area for the synthesis. A droplet elevator could be used to provide synthesis on multiple vertically stacked levels.

A cleaning or decontamination mechanism may be included in the lab-on-the-chip to rinse, wash, or otherwise decontaminate certain or all grid locations that have had or will have a component present thereon. For example, an amount (e.g., droplet) of cleaning solution (e.g., hydrogen peroxide) can be applied to and moved across the platform to cleanse the platform. In one particular example, the cleaning solution can follow immediately behind, e.g., a base symbol, thus cleaning and decontaminating the surface of any oligo that may remain. In another particular example, the cleaning solution can trace the path the oligo will follow.

Figure 5A:
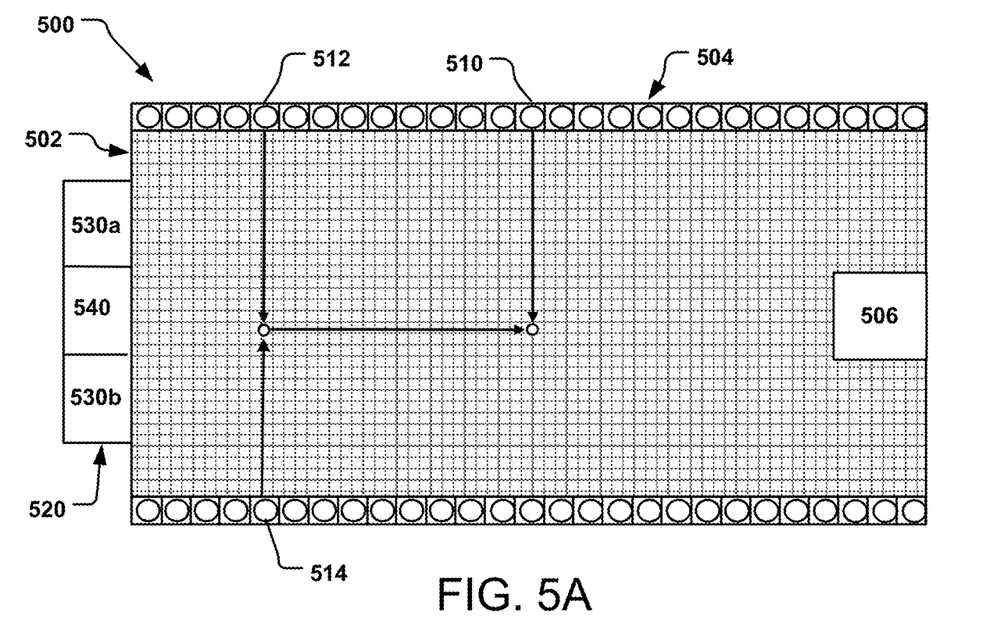
FIG. 5A is a schematic diagram of a lab-on-a-chip showing steps in a method of inserting data-encoding oligo symbols into a DNA backbone.
Figure 5B:
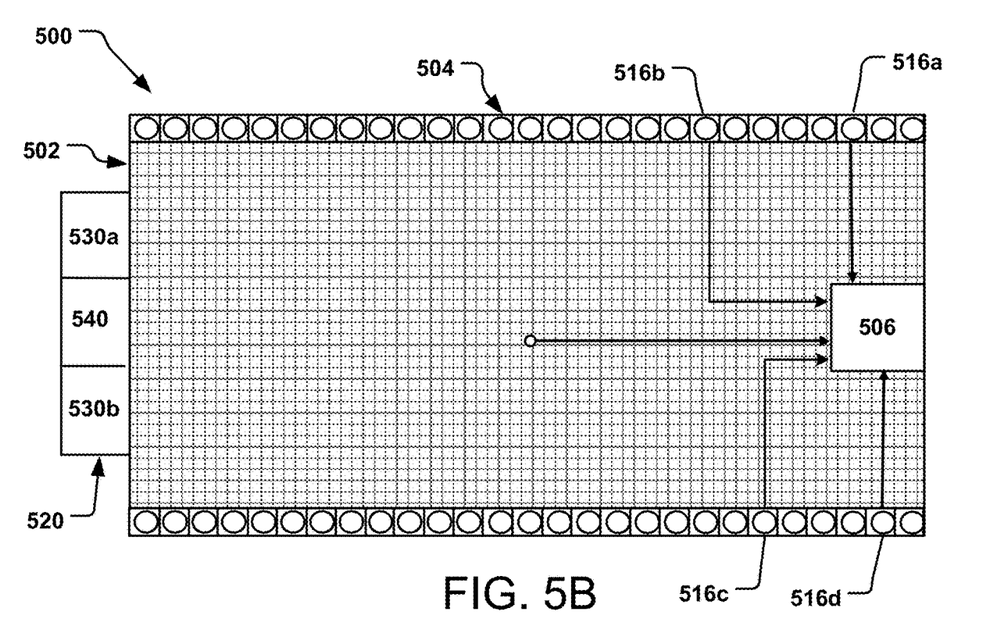
FIG. 5B is a schematic diagram of the lab-on-a-chip showing another step in the method.

FIGS. 5A and 5B illustrate two steps of an example synthesis method.

FIGS. 5A and 5B show a lab-on-a-chip 500 with a platform working surface 502 having numerous cells each configured for independently receiving a voltage. The lab 500 includes a plurality of wells 504 for the components. Although the figures show the wells 504 on two opposite sides of the platform 502, the wells 504 may be arranged on the chip 500 in any location and in any order. The lab 500 also has a final mixing location 506 for the final mixing or synthesis step (e.g., shown in FIG. 3C or FIG. 4D) for the data storage gene.

In a first step, shown in FIG. 5A, a Cas9 protein from the well 512 is combined at a first location on the platform 502 with a gRNA molecule from the well 514. The selected components (e.g., Cas9 protein, gRNA) are moved via voltage on the platform 502 to meet and combine. In a second step, also shown in FIG. 5A, the combined Cas9-gRNA is moved to a second location where it is mixed with DNA backbone from the well 510. At this second location, the Cas9-gRNA cleaves the DNA backbone.

In FIG. 5B, the cleaved backbone segments are moved to the final mixing location 506 where, in this example, four data-encoding symbols from four wells 516a, 516b, 516c, 516d are mixed with the backbone segments. After mixing, the result is a reunited DNA strand with the data-encoding symbol inserted into the strand.

The lab 500 also includes a PCR region 520 to replenish the linker and/or symbol libraries, the PCR region 520 including wells for PCR chemicals 530a, 530b and a PCR station 540. As the data-encoding symbols are depleted with each synthesized strand, occasionally, the symbols need to be replenished; the PCR region 520 of the lab 500 allows this replenishment to be done at the lab 500.

Because of the need to move numerous components, including the symbols, across the platform 502, to the final mixing location 506, and to the PCR region 520, many of which are moved or moving simultaneously, numerous paths are used. For example, at a point in time, one hundred symbols, at least one of which is a unique symbol, may be moving on the platform 502 as well as the segment backbone. In most implementations, these paths are not constrained by channels or other physical or set paths on the platform 502, but movement of the fluids on the platform 502 is controlled merely by the applied voltage. It is noted that due to the large number of paths needed, a very detailed and complicated traffic map may be needed.

The above specification and examples provide a complete description of the structure and use of exemplary implementations of the invention. The above description provides specific implementations. It is to be understood that other implementations are contemplated and may be made without departing from the scope or spirit of the present disclosure. The above detailed description, therefore, is not to be taken in a limiting sense. While the present disclosure is not so limited, an appreciation of various aspects of the disclosure will be gained through a discussion of the examples provided.

Unless otherwise indicated, all numbers expressing feature sizes, amounts, and physical properties are to be understood as being modified by the term "about," whether or not the term "about" is immediately present. Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass implementations having plural referents, unless the content clearly dictates otherwise. As used in this specification and the appended claims, the term "or" is generally employed in its sense including "and/or" unless the content clearly dictates otherwise.

Spatially related terms, including but not limited to, "bottom," "lower", "top", "upper", "beneath", "below", "above", "on top", "on," etc., if used herein, are utilized for ease of description to describe spatial relationships of an element(s) to another. Such spatially related terms encompass different orientations of the device in addition to the particular orientations depicted in the figures and described herein. For example, if a structure depicted in the figures is turned over or flipped over, portions previously described as below or beneath other elements would then be above or over those other elements.

Since many implementations of the invention can be made without departing from the spirit and scope of the invention, the invention resides in the claims hereinafter appended. Furthermore, structural features of the different implementations may be combined in yet another implementation without departing from the recited claims.

What is claimed is:

1. A method of synthesizing a DNA strand encoding data, the method comprising:
   cleaving a DNA backbone having multiple PAM sequences into multiple segments, by moving, via voltage, at least one of the DNA backbone and a set of Cas9 proteins combined with a set of gRNAs across a hydrophobic fluidic platform comprising multiple cells each configured to independently receive a voltage, and combining on the platform the DNA backbone and the set of Cas9 proteins combined with the set of gRNAs at a first location on the platform, resulting in the multiple segments each having terminal ends;
   moving across the platform to a second location on the platform, via voltage applied to individual cells, a plurality of data-encoding symbols having terminal ends on the platform;
   inserting the symbols between the multiple segments using a homology-directed repair (HDR) process, and
   joining the terminal ends of the segments to homologous terminal ends of the symbols in the presence of a ligase or a ligase with a polymerase using another homology-directed repair (HDR) process and forming the DNA strand encoding data comprising alternating segments and symbols.

2. The method of claim 1 comprising moving simultaneously across the platform at least one hundred data-encoding symbols.

3. The method of claim 2, wherein at least one of the at least one hundred symbols is unique.

4. The method of claim 1, wherein inserting the symbols between the multiple segments comprises inserting more than one symbol between two segments.

5. The method of claim 1 further comprising:
   cleaving the DNA strand encoding data comprising alternating segments and symbols into multiple second segments by moving, via voltage, the DNA strand encoding data or a second set of Cas9 proteins combined with a second set of gRNAs across the platform and combining on the platform the DNA strand encoding data and the second set of Cas9 proteins combined with the second set of gRNAs resulting in multiple second segments each having terminal ends;
   moving across the platform, via voltage, a second plurality of data-encoding symbols having terminal ends on the platform;
   inserting the second symbols between the multiple second segments, and
   joining the terminal ends of the second segments to homologous terminal ends of the second symbols and forming a second DNA strand encoding data.

6. The method of claim 1, wherein implementing the HDR process comprises implementing a Gibson assembly process.

7. The method of claim 1, wherein implementing the HDR process comprises implementing a polymerase chain reaction (PCR) assembly process.

8. The method of claim 1, wherein inserting the symbols between the multiple segments and joining the terminal ends of the segments to homologous terminal ends of the symbols comprises implementing a ligation process.

* * * * *